US009031428B2

(12) United States Patent
Fujimori et al.

(10) Patent No.: US 9,031,428 B2
(45) Date of Patent: May 12, 2015

(54) IMAGE FORMING APPARATUS CAPABLE OF DETERMINING A TONER ADHESION QUANTITY

(71) Applicants: Kohta Fujimori, Kanagawa (JP); Kayoko Tanaka, Tokyo (JP); Keita Sone, Kanagawa (JP)

(72) Inventors: Kohta Fujimori, Kanagawa (JP); Kayoko Tanaka, Tokyo (JP); Keita Sone, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 39 days.

(21) Appl. No.: 13/707,797

(22) Filed: Dec. 7, 2012

(65) Prior Publication Data
US 2013/0156449 A1 Jun. 20, 2013

(30) Foreign Application Priority Data

Dec. 14, 2011 (JP) ................................. 2011-273921

(51) Int. Cl.
G03G 15/00 (2006.01)
G01N 21/55 (2014.01)
G03G 15/01 (2006.01)

(52) U.S. Cl.
CPC ................ *G03G 15/55* (2013.01); *G01N 21/55* (2013.01); *G03G 15/0189* (2013.01); *G03G 15/5058* (2013.01)

(58) Field of Classification Search
None
See application file for complete search history.

(56) References Cited

U.S. PATENT DOCUMENTS

| 6,160,569 | A | 12/2000 | Fujimori et al. | |
|---|---|---|---|---|
| 6,181,892 | B1 | 1/2001 | Fujimori | |
| 6,243,542 | B1 * | 6/2001 | Fujimoto et al. | 399/49 |
| 7,162,171 | B2 * | 1/2007 | Sugiyama | 399/49 |
| 2002/0003975 | A1 | 1/2002 | Fujimori | |
| 2002/0118976 | A1 * | 8/2002 | Fischer | 399/49 |
| 2007/0025748 | A1 | 2/2007 | Ishibashi et al. | |
| 2007/0140721 | A1 * | 6/2007 | Shinohara et al. | 399/72 |
| 2007/0230979 | A1 | 10/2007 | Hasegawa et al. | |
| 2008/0025742 | A1 | 1/2008 | Kato et al. | |
| 2008/0031646 | A1 | 2/2008 | Ishibashi et al. | |
| 2008/0089706 | A1 * | 4/2008 | Nakazato et al. | 399/44 |
| 2008/0124107 | A1 | 5/2008 | Takeuchi et al. | |
| 2008/0145078 | A1 | 6/2008 | Tomita et al. | |
| 2008/0253793 | A1 | 10/2008 | Ishibashi et al. | |

(Continued)

FOREIGN PATENT DOCUMENTS

| JP | 6-175452 | 6/1994 |
|---|---|---|
| JP | 9-211911 | 8/1997 |

(Continued)

*Primary Examiner* — Walter L Lindsay, Jr.
*Assistant Examiner* — Arlene Heredia Ocasio
(74) *Attorney, Agent, or Firm* — Oblon, McClelland, Maier & Neustadt, L.L.P.

(57) ABSTRACT

An image forming apparatus includes a image forming unit; an image bearing member having a surface to bear a toner image and a test pattern; the surface having a first time-surface positioned identical to the test pattern, an integer multiple of revolutions upstream or downstream from the test pattern in a surface movement direction, and a second time-surface positioned different from the test pattern, shorter than one revolution upstream or downstream from the test pattern; a reflection light detector to detect the amount of light reflected from the test pattern and the first and second time-surfaces of the image bearing member; and a controller to control the image forming unit based on the detection result and determine whether to execute a first-surface control to detect at least the first time-surface or a second-surface control to detect only the second time-surface based on use condition of the image forming apparatus.

9 Claims, 7 Drawing Sheets

(56) References Cited

U.S. PATENT DOCUMENTS

| | | |
|---|---|---|
| 2009/0263150 A1 | 10/2009 | Fujimori et al. |
| 2009/0297190 A1* | 12/2009 | Kinukawa et al. .............. 399/49 |
| 2009/0324267 A1 | 12/2009 | Yoshida et al. |
| 2010/0278549 A1 | 11/2010 | Ishibashi et al. |
| 2011/0052229 A1* | 3/2011 | Shishikura et al. ............ 399/49 |
| 2012/0051771 A1* | 3/2012 | Honda ............................ 399/49 |
| 2012/0237233 A1* | 9/2012 | Kato et al. ..................... 399/49 |
| 2012/0294637 A1 | 11/2012 | Tanaka et al. |
| 2013/0156449 A1* | 6/2013 | Fujimori et al. ................ 399/44 |

FOREIGN PATENT DOCUMENTS

| | | |
|---|---|---|
| JP | 2006-150627 | 6/2006 |
| JP | 2009-150963 | 7/2009 |
| JP | 2009-288351 | 12/2009 |
| JP | 2010-009018 | 1/2010 |
| JP | 2012-093538 | 5/2012 |
| JP | 2012-194408 | 10/2012 |

* cited by examiner

FIG. 8A

| ABSOLUTE HUMIDITY (g/m^3) | | RELATIVE HUMIDITY (%RH) | | | | | | | |
|---|---|---|---|---|---|---|---|---|---|
| | | 5 | 10 | 15 | 20 | 25 | 30 | 35 | 40 | 45 |
| TEMPERATURE (°C) | -5 | 0.17 | 0.34 | 0.51 | 0.68 | 0.85 | 1.02 | 1.19 | 1.36 | 1.53 |
| | -4 | 0.18 | 0.37 | 0.55 | 0.73 | 0.92 | 1.10 | 1.28 | 1.47 | 1.65 |
| | -3 | 0.20 | 0.39 | 0.59 | 0.79 | 0.98 | 1.18 | 1.38 | 1.57 | 1.77 |
| | -2 | 0.21 | 0.42 | 0.63 | 0.84 | 1.06 | 1.27 | 1.48 | 1.69 | 1.90 |
| | -1 | 0.23 | 0.45 | 0.68 | 0.91 | 1.13 | 1.36 | 1.58 | 1.81 | 2.04 |
| | 0 | 0.24 | 0.49 | 0.73 | 0.97 | 1.21 | 1.46 | 1.70 | 1.94 | 2.18 |
| | 1 | 0.26 | 0.52 | 0.78 | 1.04 | 1.30 | 1.56 | 1.82 | 2.08 | 2.34 |
| | 2 | 0.28 | 0.56 | 0.84 | 1.11 | 1.39 | 1.67 | 1.95 | 2.23 | 2.51 |
| | 3 | 0.30 | 0.60 | 0.89 | 1.19 | 1.49 | 1.79 | 2.08 | 2.38 | 2.68 |
| | 4 | 0.32 | 0.64 | 0.96 | 1.27 | 1.59 | 1.91 | 2.23 | 2.55 | 2.87 |
| | 5 | 0.34 | 0.68 | 1.02 | 1.36 | 1.70 | 2.04 | 2.38 | 2.72 | 3.06 |
| | 6 | 0.36 | 0.73 | 1.09 | 1.45 | 1.82 | 2.18 | 2.55 | 2.91 | 3.27 |
| | 7 | 0.39 | 0.78 | 1.16 | 1.55 | 1.94 | 2.33 | 2.72 | 3.11 | 3.49 |
| | 8 | 0.41 | 0.83 | 1.24 | 1.66 | 2.07 | 2.48 | 2.90 | 3.31 | 3.73 |
| | 9 | 0.44 | 0.88 | 1.32 | 1.77 | 2.21 | 2.65 | 3.09 | 3.53 | 3.97 |
| | 10 | 0.47 | 0.94 | 1.41 | 1.88 | 2.35 | 2.82 | 3.29 | 3.77 | 4.24 |
| | 11 | 0.50 | 1.00 | 1.50 | 2.01 | 2.51 | 3.01 | 3.51 | 4.01 | 4.51 |
| | 12 | 0.53 | 1.07 | 1.60 | 2.14 | 2.67 | 3.20 | 3.74 | 4.27 | 4.80 |
| | 13 | 0.57 | 1.14 | 1.70 | 2.27 | 2.84 | 3.41 | 3.98 | 4.54 | 5.11 |
| | 14 | 0.60 | 1.21 | 1.81 | 2.42 | 3.02 | 3.63 | 4.23 | 4.83 | 5.44 |
| | 15 | 0.64 | 1.28 | 1.93 | 2.57 | 3.21 | 3.85 | 4.50 | 5.14 | 5.78 |
| | 16 | 0.68 | 1.36 | 2.05 | 2.73 | 3.41 | 4.09 | 4.78 | 5.46 | 6.14 |
| | 17 | 0.72 | 1.45 | 2.17 | 2.90 | 3.62 | 4.35 | 5.07 | 5.80 | 6.52 |
| | 18 | 0.77 | 1.54 | 2.31 | 3.08 | 3.85 | 4.62 | 5.39 | 6.16 | 6.92 |
| | 19 | 0.82 | 1.63 | 2.45 | 3.27 | 4.08 | 4.90 | 5.71 | 6.53 | 7.35 |
| | 20 | 0.87 | 1.73 | 2.60 | 3.46 | 4.33 | 5.19 | 6.06 | 6.93 | 7.79 |
| | 21 | 0.92 | 1.84 | 2.75 | 3.67 | 4.59 | 5.51 | 6.42 | 7.34 | 8.26 |
| | 22 | 0.97 | 1.94 | 2.92 | 3.89 | 4.86 | 5.83 | 6.81 | 7.78 | 8.75 |
| | 23 | 1.03 | 2.06 | 3.09 | 4.12 | 5.15 | 6.18 | 7.21 | 8.24 | 9.27 |
| | 24 | 1.09 | 2.18 | 3.27 | 4.36 | 5.45 | 6.54 | 7.63 | 8.72 | 9.81 |
| | 25 | 1.15 | 2.31 | 3.46 | 4.61 | 5.77 | 6.92 | 8.07 | 9.22 | 10.38 |
| | 26 | 1.22 | 2.44 | 3.66 | 4.88 | 6.10 | 7.32 | 8.54 | 9.76 | 10.98 |
| | 27 | 1.29 | 2.58 | 3.87 | 5.16 | 6.45 | 7.73 | 9.02 | 10.31 | 11.60 |
| | 28 | 1.36 | 2.72 | 4.09 | 5.45 | 6.81 | 8.17 | 9.54 | 10.90 | 12.26 |
| | 29 | 1.44 | 2.88 | 4.32 | 5.76 | 7.19 | 8.63 | 10.07 | 11.51 | 12.95 |
| | 30 | 1.52 | 3.04 | 4.56 | 6.08 | 7.60 | 9.11 | 10.63 | 12.15 | 13.67 |
| | 31 | 1.60 | 3.21 | 4.81 | 6.41 | 8.02 | 9.62 | 11.22 | 12.82 | 14.43 |
| | 32 | 1.69 | 3.38 | 5.07 | 6.76 | 8.46 | 10.15 | 11.84 | 13.53 | 15.22 |
| | 33 | 1.78 | 3.57 | 5.35 | 7.13 | 8.92 | 10.70 | 12.48 | 14.27 | 16.05 |
| | 34 | 1.88 | 3.76 | 5.64 | 7.52 | 9.40 | 11.28 | 13.16 | 15.04 | 16.92 |
| | 35 | 1.98 | 3.96 | 5.94 | 7.92 | 9.90 | 11.88 | 13.86 | 15.84 | 17.82 |
| | 36 | 2.09 | 4.17 | 6.26 | 8.34 | 10.43 | 12.51 | 14.60 | 16.68 | 18.77 |
| | 37 | 2.20 | 4.39 | 6.59 | 8.78 | 10.98 | 13.17 | 15.37 | 17.57 | 19.76 |
| | 38 | 2.31 | 4.62 | 6.93 | 9.24 | 11.55 | 13.86 | 16.17 | 18.49 | 20.80 |
| | 39 | 2.43 | 4.86 | 7.29 | 9.72 | 12.15 | 14.58 | 17.02 | 19.45 | 21.88 |
| | 40 | 2.56 | 5.11 | 7.67 | 10.22 | 12.78 | 15.34 | 17.89 | 20.45 | 23.00 |
| | 41 | 2.69 | 5.37 | 8.06 | 10.75 | 13.43 | 16.12 | 18.81 | 21.50 | 24.18 |
| | 42 | 2.82 | 5.65 | 8.47 | 11.29 | 14.12 | 16.94 | 19.76 | 22.59 | 25.41 |
| | 43 | 2.97 | 5.93 | 8.90 | 11.86 | 14.83 | 17.79 | 20.76 | 23.73 | 26.69 |
| | 44 | 3.11 | 6.23 | 9.34 | 12.46 | 15.57 | 18.68 | 21.80 | 24.91 | 28.03 |
| | 45 | 3.27 | 6.54 | 9.81 | 13.07 | 16.34 | 19.61 | 22.88 | 26.15 | 29.42 |

FIG. 8B

| 50 | 55 | 60 | 65 | 70 | 75 | 80 | 85 | 90 | 95 |
|---|---|---|---|---|---|---|---|---|---|
| 1.70 | 1.88 | 2.05 | 2.22 | 2.39 | 2.56 | 2.73 | 2.90 | 3.07 | 3.24 |
| 1.83 | 2.02 | 2.20 | 2.38 | 2.56 | 2.75 | 2.93 | 3.11 | 3.30 | 3.48 |
| 1.97 | 2.16 | 2.36 | 2.56 | 2.75 | 2.95 | 3.15 | 3.34 | 3.54 | 3.74 |
| 2.11 | 2.32 | 2.53 | 2.74 | 2.96 | 3.17 | 3.38 | 3.59 | 3.80 | 4.01 |
| 2.26 | 2.49 | 2.72 | 2.94 | 3.17 | 3.40 | 3.62 | 3.85 | 4.08 | 4.30 |
| 2.43 | 2.67 | 2.91 | 3.16 | 3.40 | 3.64 | 3.88 | 4.13 | 4.37 | 4.61 |
| 2.60 | 2.86 | 3.12 | 3.38 | 3.64 | 3.90 | 4.16 | 4.42 | 4.68 | 4.94 |
| 2.78 | 3.06 | 3.34 | 3.62 | 3.90 | 4.18 | 4.45 | 4.73 | 5.01 | 5.29 |
| 2.98 | 3.28 | 3.57 | 3.87 | 4.17 | 4.47 | 4.77 | 5.06 | 5.36 | 5.66 |
| 3.18 | 3.50 | 3.82 | 4.14 | 4.46 | 4.78 | 5.10 | 5.41 | 5.73 | 6.05 |
| 3.40 | 3.74 | 4.08 | 4.42 | 4.77 | 5.11 | 5.45 | 5.79 | 6.13 | 6.47 |
| 3.64 | 4.00 | 4.36 | 4.73 | 5.09 | 5.45 | 5.82 | 6.18 | 6.54 | 6.91 |
| 3.88 | 4.27 | 4.66 | 5.05 | 5.43 | 5.82 | 6.21 | 6.60 | 6.99 | 7.37 |
| 4.14 | 4.56 | 4.97 | 5.38 | 5.80 | 6.21 | 6.63 | 7.04 | 7.45 | 7.87 |
| 4.42 | 4.86 | 5.30 | 5.74 | 6.18 | 6.62 | 7.07 | 7.51 | 7.95 | 8.39 |
| 4.71 | 5.18 | 5.65 | 6.12 | 6.59 | 7.06 | 7.53 | 8.00 | 8.47 | 8.94 |
| 5.01 | 5.52 | 6.02 | 6.52 | 7.02 | 7.52 | 8.02 | 8.52 | 9.03 | 9.53 |
| 5.34 | 5.87 | 6.41 | 6.94 | 7.47 | 8.01 | 8.54 | 9.08 | 9.61 | 10.14 |
| 5.68 | 6.25 | 6.82 | 7.39 | 7.95 | 8.52 | 9.09 | 9.66 | 10.23 | 10.79 |
| 6.04 | 6.65 | 7.25 | 7.85 | 8.46 | 9.06 | 9.67 | 10.27 | 10.88 | 11.48 |
| 6.42 | 7.07 | 7.71 | 8.35 | 8.99 | 9.63 | 10.28 | 10.92 | 11.56 | 12.20 |
| 6.82 | 7.51 | 8.19 | 8.87 | 9.55 | 10.24 | 10.92 | 11.60 | 12.28 | 12.97 |
| 7.25 | 7.97 | 8.70 | 9.42 | 10.15 | 10.87 | 11.60 | 12.32 | 13.05 | 13.77 |
| 7.69 | 8.46 | 9.23 | 10.00 | 10.77 | 11.54 | 12.31 | 13.08 | 13.85 | 14.62 |
| 8.16 | 8.98 | 9.80 | 10.61 | 11.43 | 12.24 | 13.06 | 13.88 | 14.69 | 15.51 |
| 8.66 | 9.52 | 10.39 | 11.25 | 12.12 | 12.99 | 13.85 | 14.72 | 15.58 | 16.45 |
| 9.18 | 10.09 | 11.01 | 11.93 | 12.85 | 13.76 | 14.68 | 15.60 | 16.52 | 17.43 |
| 9.72 | 10.69 | 11.67 | 12.64 | 13.61 | 14.58 | 15.56 | 16.53 | 17.50 | 18.47 |
| 10.30 | 11.33 | 12.35 | 13.38 | 14.41 | 15.44 | 16.47 | 17.50 | 18.53 | 19.56 |
| 10.90 | 11.99 | 13.08 | 14.17 | 15.26 | 16.35 | 17.44 | 18.53 | 19.62 | 20.71 |
| 11.53 | 12.68 | 13.84 | 14.99 | 16.14 | 17.30 | 18.45 | 19.60 | 20.76 | 21.91 |
| 12.20 | 13.41 | 14.63 | 15.85 | 17.07 | 18.29 | 19.51 | 20.73 | 21.95 | 23.17 |
| 12.89 | 14.18 | 15.47 | 1.76 | 18.05 | 19.34 | 20.63 | 21.92 | 23.20 | 24.49 |
| 13.62 | 14.98 | 16.35 | 17.71 | 19.07 | 20.43 | 21.80 | 23.16 | 24.52 | 25.88 |
| 14.39 | 15.83 | 17.27 | 18.70 | 20.14 | 21.58 | 23.02 | 24.46 | 25.90 | 27.34 |
| 15.19 | 16.71 | 18.23 | 19.75 | 21.27 | 22.79 | 24.30 | 25.82 | 27.34 | 28.86 |
| 16.03 | 17.63 | 19.24 | 20.84 | 22.44 | 24.05 | 25.65 | 27.25 | 28.86 | 30.46 |
| 16.91 | 18.60 | 20.29 | 21.98 | 23.67 | 25.37 | 27.06 | 28.75 | 30.44 | 32.13 |
| 17.83 | 19.61 | 21.40 | 23.18 | 24.96 | 26.75 | 28.53 | 30.31 | 32.10 | 33.88 |
| 18.79 | 20.67 | 22.55 | 24.43 | 26.31 | 28.19 | 30.07 | 31.96 | 33.83 | 35.71 |
| 19.80 | 21.78 | 23.76 | 25.74 | 27.72 | 29.70 | 31.68 | 33.66 | 35.64 | 37.62 |
| 20.86 | 22.94 | 25.03 | 27.11 | 29.20 | 31.28 | 33.37 | 35.45 | 37.54 | 39.63 |
| 21.96 | 24.15 | 26.35 | 28.54 | 30.74 | 32.93 | 35.13 | 37.33 | 39.52 | 41.72 |
| 23.11 | 25.42 | 27.73 | 30.04 | 32.35 | 34.66 | 36.97 | 39.28 | 41.59 | 43.90 |
| 24.31 | 26.74 | 29.17 | 31.60 | 34.03 | 36.46 | 38.89 | 41.32 | 43.75 | 46.18 |
| 25.56 | 28.12 | 30.67 | 33.23 | 35.79 | 38.34 | 40.90 | 43.45 | 46.01 | 48.57 |
| 26.87 | 29.56 | 32.24 | 34.93 | 37.62 | 40.30 | 42.99 | 45.68 | 48.36 | 51.05 |
| 28.23 | 31.06 | 33.88 | 36.70 | 39.53 | 42.35 | 45.17 | 48.00 | 50.82 | 53.64 |
| 29.66 | 32.62 | 35.59 | 38.55 | 41.52 | 44.49 | 47.45 | 50.42 | 53.38 | 56.35 |
| 31.14 | 34.25 | 37.37 | 40.48 | 43.60 | 46.71 | 49.83 | 52.94 | 56.05 | 59.17 |
| 32.69 | 35.96 | 39.22 | 42.49 | 45.76 | 49.03 | 52.30 | 55.57 | 58.84 | 62.11 |

IMAGE FORMING APPARATUS CAPABLE OF DETERMINING A TONER ADHESION QUANTITY

CROSS-REFERENCE TO RELATED APPLICATION

This patent application is based on and claims priority pursuant to 35 U.S.C. §119 to Japanese Patent Application No. 2011-273921, filed on Dec. 14, 2011 in the Japan Patent Office, the entire disclosure of which is hereby incorporated by reference herein.

BACKGROUND

1. Technical Field

Exemplary aspects of this disclosure generally relate to an image forming apparatus, such as a copier, a printer, a facsimile machine, a plotter, or a multifunction machine capable of performing at least two of these functions.

2. Description of the Related Art

In electrophotographic image forming apparatuses, imaging conditions (e.g., a charging bias, a development bias, operation of an exposure device) are adjusted to maintain a certain image density. More specifically, a test toner pattern is formed on a transfer belt that bears the toner and a reflection light detector (optical detector) detects an amount of toner adhering (hereinafter toner adhesion quantity) to the test-toner pattern. Based on the detection result obtained by the optical detector, the image forming apparatus adjusts one or more of the imaging conditions in a toner-image formation unit.

After the test toner pattern is formed on the surface of the transfer belt, the reflection light detector detects not only the amount of light reflected from the test pattern but also the amount of light reflected from a clear area of the transfer belt on which the test-toner pattern is not formed. Then, the image forming apparatus compares the two readings and estimates the toner adhesion quantity of the test toner therefrom.

However, since the amount of light reflected by the belt fluctuates depending on the location, the toner adhesion quantity cannot be estimated accurately if the detected positions between the toner-adhered test pattern and the surface of the transfer belt differ.

Accordingly, in the known image forming apparatus, the amount of light reflected from the surface of the transfer belt has been detected in advance at least one revolution before, and then the test-toner pattern is formed and the amount of light reflected from the test-toner pattern is detected. Thus, the detection position where the toner-pattern output is detected and the detection position where the surface output is detected are located at the same position, which allows the toner adhesion quantity to be properly detected.

However, in the above-described apparatus, whenever the toner adhesion quantity is estimated, it is necessary to make the transfer belt rotate one revolution or more before the test-toner pattern is formed, thereby lengthening downtime. The downtime can be minimized by reducing the frequency with which the toner adhesion quantity is estimated, but doing so degrades the toner adhesion quantity estimates and imaging condition control precision deteriorates, possibly resulting in unstable image density.

In order to prevent the downtime from lengthening due to the toner adhesion quantity estimation process, it is possible to obtain the output of the surface in advance at a time when lengthening the downtime is acceptable (e.g., when the transfer belt is replaced) and using only the toner output readings to estimate the toner adhesion quantity. In this method, the toner adhesion quantity is estimated using the toner-pattern output detected and the surface output detected in the portion identical to a portion in which the test-toner pattern will be formed and stored in memory. Therefore, it is not necessary to make the transfer belt rotate one or more revolutions before the toner pattern is formed, which prevents the downtime from lengthening.

However, such previously stored information does not adequately account for the effects of changes in the amount of light reflected from the surface caused by scratches and grime generated when the transfer belt comes into contact with other parts of the apparatus and which are not reflected in the estimation operation. As a result, the toner adhesion quantity might not be estimated accurately.

Moreover, although a configuration in which the image bearing member on which the toner image is formed is the transfer belt is described above, a similar problem may occur with a drum-shaped intermediate transfer member or a belt-shaped or drum-shaped photoreceptor. Further, the toner information is not limited to that which is detected by the relation between the amounts of light reflected from the toner-adhered test pattern and that from the surface of the image bearing member directly.

BRIEF SUMMARY

In one aspect of this disclosure, there is provided a novel image forming apparatus including an endless rotary image bearing member, an image forming unit, a reflection light detector, and a controller. The endless rotary image bearing member has a surface to bear a toner image and a potential-control toner pattern. The image forming unit forms the toner image and the potential-control toner pattern onto the surface of the image bearing member. The reflection light detector has a light source to emit light onto the surface of the image bearing member and the potential-control toner pattern formed on the image bearing member and a light-receiving element to detect the amount of light reflected from the potential-control toner pattern formed on the surface of the image bearing member as toner attraction output, and the amount of light reflected from the surface of the image bearing member as a surface output. The controller detects toner information of the toner image based on the toner attraction output corresponding to the detected amount of light reflected from the potential-control toner pattern formed on the image bearing member, and the surface output corresponding to the amount of light reflected from the image bearing member. The controller controls the toner image forming unit based on the detected toner information. The surface output includes a first surface output and a second surface output. The first surface output is detected from a first time-surface of the image bearing member positioned identical to the potential-control toner pattern. The first time-surface is positioned one of an integer multiple of revolutions upstream from the potential-control toner pattern in a surface movement direction in which the surface of the image bearing member is moved and an integer multiple of revolutions downstream from the potential-control toner pattern in the surface movement direction. The second surface output is detected from a second time-surface of the image bearing member positioned different from the potential-control toner pattern. The second time-surface is positioned at a location shorter than one revolution upstream or from the potential-control toner pattern in the surface movement direction. The controller determines whether to execute a first-surface output control, during which the reflection light detector detects at least the first time-surface of the image bearing member, or a second-surface output control, during which the reflection light detector detects only the second time-surface of the image bearing member, based on use condition of the image forming apparatus.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIGS. 8A and 8B are one example of calculation table to acquire the absolute humidity.

DETAILED DESCRIPTION OF PREFERRED EMBODIMENTS

Figure 1:
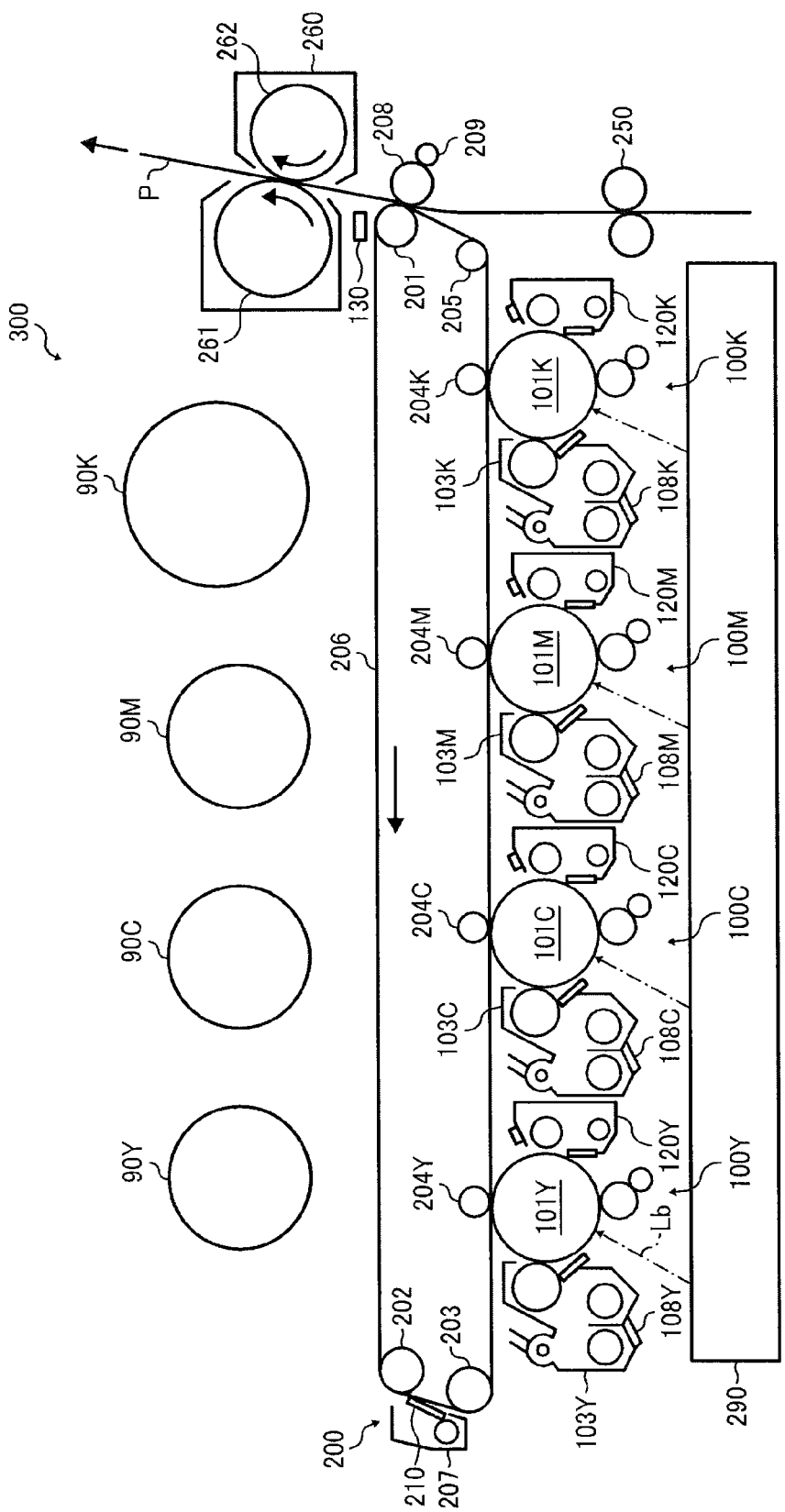
FIG. 1 is a schematic configuration diagram illustrating major components of a printer according to the present disclosure.

In describing preferred embodiments illustrated in the drawings, specific terminology is employed for the sake of clarity. However, the disclosure of this patent specification is not intended to be limited to the specific terminology so selected, and it is to be understood that each specific element includes all technical equivalents that have the same function, operate in a similar manner, and achieve a similar result. Referring now to the drawings, wherein like reference numerals designate identical or corresponding parts throughout the several views thereof, and particularly to FIGS. 1 through 8B, an electrophotographic image forming apparatus according to illustrative embodiments of the present disclosure is described.

FIG. 1 is a schematic diagram illustrating a tandem-type color copier as an example of a printer 300 according to an aspect of this disclosure. It is to be noted that the configuration of the present specification is not limited to that shown in FIG. 1. For example, the configuration of the present specification may be adapted to printers including an electrophotographic image forming device as well as other types of image forming apparatuses, such as copiers, facsimile machines, multifunction peripherals (MFP), and the like. When the image forming apparatus 100 is used as the printer or the facsimile, an image forming process is executed based on image signal corresponding to image data received from outside.

The printer 300 includes, in addition to the configurations illustrated in FIG. 1, not-illustrated components, such as a print controller or processor for processing image data transmitted from, for example, a personal computer (hereinafter referred to as PC) and converting the image data into exposure data, a high-voltage generating device for generating a relatively high voltage, a later-described control unit 500 (see FIG. 5) for controlling an image forming operation, a sheet feeding device for supplying a recording sheet P serving as a recording medium, a manual feed tray from which a recording sheet P is manually fed, and a sheet discharge tray to which an image-formed recording sheet P is discharged.

In FIG. 1, a reference numeral 200 denotes a transfer unit serving as a transfer device. The transfer unit 200 includes a drive roller 201, a cleaning backup roller 202, a primary transfer nip entrance roller 203, four primary transfer rollers 204Y, 204C, 204M, and 204K, a secondary transfer nip entrance roller 205, an intermediate transfer belt 206, a belt cleaning device 207 including a cleaning blade 210, a secondary transfer roller 208, and a cleaning roller 209. As the drive roller 201 is driven to rotate, the endless intermediate transfer belt 206 serving as an endless belt member is rotated in the counterclockwise direction in FIG. 1, while being stretched by a plurality of rollers provided inside a loop of the intermediate transfer belt 206. Suffixes Y, C, M, and K following the reference numeral 204 denoting the four primary transfer rollers 204Y, 204C, 204M, and 204K indicate that the members attached with the suffixes are for yellow, cyan, magenta, and black colors. The same applies to the suffixes Y, C, M, and K following other reference numerals.

The intermediate transfer belt 206 has a three-layer structure including a belt base layer, an elastic layer, and a surface layer, with the elastic layer and the surface layer sequentially laminated on the outer surface of the belt base layer which is the thickest among the three layers. The belt base layer is made of, for example, a material combining a relatively inelastic fluorine-based resin, a substantially elastic rubber material, and a relatively non-stretchable material such as canvas. The elastic layer is made of, for example, a fluorine-based rubber or an acrylonitrile-butadiene copolymer rubber, and is laminated on the outer surface of the belt base layer. The surface layer is made of, for example, a fluorine-based resin applied to the outer surface of the elastic layer to coat the surface.

Below the transfer unit 200, four image forming units 100Y, 100C, 100M, and 100K for the Y, C, M, and K colors are provided in a line along a lower stretched surface of the intermediate transfer belt 206. The image forming units 100Y, 100C, 100M, and 100K include drum-like photoconductors 101Y, 101C, 101M, and 101K, charging devices 102Y, 102C, 102M, and 102K, development devices 103Y, 103C, 103M, and 103K, and drum cleaning devices 120Y, 120C, 120M, and 120K, respectively. The respective top portions of the outer circumferential surfaces of the photoconductors 101Y, 101C, 101M, and 101K are brought into contact with the lower stretched surface of the intermediate transfer belt 206 to from primary transfer nips for the Y, C, M, and K colors.

Above the transfer unit 200, toner bottles 90Y, 90C, 90M, and 90K for the Y, C, M, and K colors respectively containing not-illustrated Y, C, M, and K toners are provided in a line along an upper stretched surface of the intermediate transfer belt 206. The Y, C, M, and K toners contained in the toner bottles 90Y, 90C, 90M, and 90K are supplied to the development devices 103Y, 103C, 103M, and 103K, respectively, in accordance with driving of not-illustrated toner replenishing devices for the Y, C, M, and K colors. Each of the toner bottles 90Y, 90C, 90M, and 90K is individually attachable to and detachable from the body of the printer 300 serving as the image forming apparatus, and is replaced by a new toner bottle when running out of the toner contained therein.

Below the four image forming units 100Y, 100C, 100M, and 100K aligned along the lower stretched surface of the intermediate transfer belt 206, an optical writing unit 290 is provided. On the basis of image information, the optical writing unit 290 drives not-illustrated semiconductor lasers provided therein to emit writing light Lb for each of the Y, C, M, and K colors. With the writing light Lb, the optical writing unit 290 then optically scans the photoconductors 101Y, 101C, 101M, and 101K serving as latent image carrying members, and thereby writes electrostatic latent images on the outer circumferential surfaces of the photoconductors 101Y, 101C, 101M, and 101K driven to rotate in the clockwise direction in FIG. 1. The light sources of the writing light Lb are not limited to the semiconductor lasers, and may be light emitting diodes (LEDs), for example.

A configuration of the image forming units 100Y, 100C, 100M, and 100K will now be described with reference to the image forming unit 100K for the K color as an example. The image forming units 100Y, 100C, and 100M for the other colors of Y, C, and M are similar in configuration to the image forming unit 100K for the K color except for the difference in color of the toner used therein, and thus description thereof will be omitted.

Figure 2:
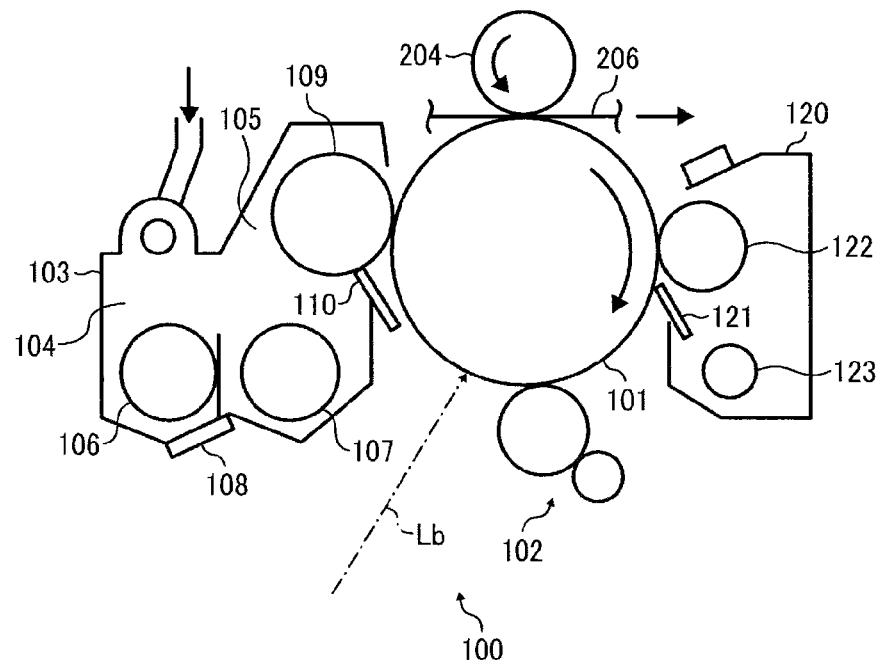
FIG. 2 is an enlarged configuration diagram illustrating an image forming unit included in the printer.

FIG. 2 is an enlarged configuration diagram illustrating the image forming unit 100 in the printer 300. It is to be noted that the suffixes Y, M, C, and K indicate only that components indicated thereby are used for forming yellow, magenta, cyan, and black images, respectively, and hereinafter may be omitted when color discrimination is not necessary. In the image forming unit 100, the drum-like photoconductor 101 is surrounded by, for example, the charging device 102 for uniformly charging the photoconductor 101, the development device 103, and the drum cleaning device 120.

The charging device 102 is based on a contact charging method that brings a charge roller applied with a charging bias by a not-illustrated power supply into contact with the photoconductor 101. The charging device 102 uniformly charges the outer circumferential surface of the photoconductor 101 by causing discharge between the charge roller and the photoconductor 101. The contact charging method employing the charge roller may be replaced by a contact discharge method employing a charge brush or a non-contact charging method employing a scorotron charger.

The development device 103 has a casing housing a mixing section 104 for mixing a two-component developer containing not-illustrated magnetic carrier and non-magnetic toner and a development section 105 housing a later-described development sleeve 109. In the mixing section 104, the two-component developer (hereinafter simply referred to as the developer) is conveyed while being mixed. More specifically, the mixing section 104 includes a first screw member 106 and a second screw member 107 provided parallel to each other and a divider plate provided therebetween. The divider plate divides the space housing the first and second screw members 106 and 107 into two spaces. Opposite end portions of the divider plate in the axial direction of the first and second screw members 106 and 107 are respectively formed with openings. Thereby, the two spaces communicate with each other at the opposite end portions of the divider plate in the axial direction of the first and second screw members 106 and 107. Hereinafter, the space housing the first screw member 106 and the space housing the second screw member 107 will be referred to as the first mixing chamber and the second mixing chamber, respectively.

The second screw member 107 is located under the development section 105. The upper end side of the outer circumferential surface of the second screw member 107 faces the lower end side of the development sleeve 109 housed in the development section 105. The second screw member 107 is driven to rotate by a not-illustrated drive device, and conveys the developer in the second mixing chamber from the far side toward the near side in a direction perpendicular to the drawing plane. In this process, the second screw member 107 supplies the developer to the development sleeve 109 and receives the used developer from the development sleeve 109. The developer conveyed by the second screw member 107 to an end portion on the near side in FIG. 2 enters the first mixing chamber through the corresponding opening of the divider plate.

The first screw member 106 is driven to rotate by a not-illustrated drive device, and conveys the developer in the first mixing chamber from the near side toward the far side in the direction perpendicular to the drawing plane. A bottom wall of the first mixing chamber is fixed with a toner concentration sensor 108 that detects the toner concentration of the developer conveyed by the first screw member 106. The result of the detection is transmitted to the not-illustrated control unit 500 (see FIG. 5) as a toner concentration signal. The control unit 500 drives, as appropriate, the not-illustrated toner replenishing device on the basis of the toner concentration signal, to replenish the first mixing chamber with an appropriate amount of toner. Thereby, the toner concentration of the developer, which has been reduced in accordance with the development performed in the development section 105, is increased. The developer conveyed by the first screw member 106 to an end portion on the far side in FIG. 2 enters the second mixing chamber through the other opening provided in the divider plate. Thereby, the developer in the development device 103 is circularly conveyed along a route from the first mixing chamber to the second mixing chamber, the development section 105, the second mixing chamber, and the first mixing chamber. Accordingly, the toner concentration is adjusted in the first mixing chamber.

The development section 105 includes the cylindrical development sleeve 109 driven to rotate by a not-illustrated drive device. A portion of the outer circumferential surface of the development sleeve 109 is exposed to the outside of the casing of the development device 103 through an opening provided in the casing. The exposed portion of the development sleeve 109 faces the photoconductor 101 via a minute development gap. Further, the development sleeve 109 houses a not-illustrated magnet roller in a hollow space thereof. The magnet roller is non-rotatably fixed so as not to rotate together with the development sleeve 109.

The developer conveyed by the second screw member 107 in the above-described second mixing chamber is attracted to and carried on the outer circumferential surface of the development sleeve 109 by magnetic force generated by the magnet roller. Then, as the developer passes a gap between the developer sleeve 109 and a regulation blade 110 in accordance with the rotation of the development sleeve 109, the thickness of the layer of the developer on the development sleeve 109 is regulated. Thereafter, the developer is conveyed to a development area facing the photoconductor 101.

The development sleeve 109 made of a non-magnetic material includes therein a not-illustrated development electrode applied with a development bias. In the development area, a development electric field is generated between the electrostatic latent image on the photoconductor 101 and the development sleeve 109. The developer conveyed to the development area is caused to stand up in spikes and form a magnetic brush by magnetic force generated by a not-illustrated development magnetic pole of the magnet roller, and the leading end of the magnetic brush is brought into sliding contact with the photoconductor 101. Then, the toner in the magnetic brush separates from the magnetic carrier owing to the action of the above-described development electric field, and is transferred to the electrostatic latent image on the photoconductor 101. With this transfer, the electrostatic latent image on the photoconductor 101 is developed into a toner image as a visible image.

When the developer passes the development area and reaches a position facing the second mixing chamber in accordance with the rotation of the development sleeve 109, the developer separates from the outer circumferential surface of the development sleeve 109 and falls into the second mixing chamber owing to the action of a repulsive magnetic field generated by two not-illustrated homopolar magnetic poles of the magnet roller.

Accordingly, the toner in the developer is transferred to the electrostatic latent image on the photoconductor 101, and the electrostatic latent image on the photoconductor 101 is visualized into a toner image. The developer having passed the development area is conveyed to an area in which the magnetic force of the magnet roller is relatively weak. Thereby, the developer separates from the development sleeve 109 and returns to the mixing section 104.

Although the above description has been given of the development device 103 employing the two-component development method using the two-component developer, a development device according to a one-component development method may be employed which uses a one-component developer not containing magnetic carrier but containing toner.

In accordance with the rotation of the photoconductor 101 in the clockwise direction in FIG. 2, the toner image formed on the outer circumferential surface of the photoconductor 101 serving as an image carrying member enters the primary transfer nip formed by the contact between the photoconductor 101 and the intermediate transfer belt 206, and is primary-transferred onto the outer circumferential surface of the intermediate transfer belt 206. The outer circumferential surface of the photoconductor 101 having passed the primary transfer nip reaches a position facing the drum cleaning device 120.

The drum cleaning device 120 includes a cleaning blade 121, a conductive fur brush 122, and a discharge screw 123. The cleaning blade 121 is made of, for example, polyurethane rubber, and has a leading end pressed against the photoconductor 101. A slight amount of post-transfer residual toner having failed to be transferred to the intermediate transfer belt 206 adheres to the outer circumferential surface of the photoconductor 101 having passed the above-described primary transfer nip. The post-transfer residual toner is scraped off the outer circumferential surface of the photoconductor 101 by the cleaning blade 121 and collected in the drum cleaning device 120.

The fur brush 122 rotates while in contact with the outer circumferential surface of the photoconductor 101 at a position immediately before the position of contact between the photoconductor 101 and the cleaning blade 121. The fur brush 122 also removes the post-transfer residual toner. The toner removed from the photoconductor 101 by the cleaning blade 121 and the fur brush 122 is stored in the drum cleaning device 120, and is discharged outside the drum cleaning device 120 by the discharge screw 123. The discharged toner is then collected in a not-illustrated waste toner bottle.

In FIG. 1 described above, the outer circumferential surface of the photoconductor 101K is uniformly charged to, for example, approximately −700 V by the charging device 102K. The potential of the electrostatic latent image applied with the writing light Lb by the optical writing unit 290 is approximately −120 V, for example. Meanwhile, the development bias voltage applied to the development sleeve 109 in FIG. 2 is approximately −470 V, for example. Thereby, development potential of approximately 350 V, for example, is generated. Such an imaging condition is changed as appropriate by a later-described solid density stabilization process.

The primary transfer rollers 204Y, 204C, 204M, and 204K of the transfer unit 200 serving as primary transfer members are in contact with the inner circumferential surface of the intermediate transfer belt 206 at respective positions corresponding to the primary transfer nips for the Y, C, M, and K colors. Each of the primary transfer rollers 204Y, 204C, 204M, and 204K thus in contact with the inner circumferential surface of the intermediate transfer belt 206 is applied with a primary transfer bias by a not-illustrated power supply. In the primary transfer nips for the Y, C, M, and K colors, therefore, primary transfer electric fields are generated which electrostatically move the toner images on the photoconductors 101Y, 101C, 101M, and 101K from the outer circumferential surfaces of the photoconductors 101Y, 101C, 101M, and 101K toward the intermediate transfer belt 206. Although the present printer 300 employs the primary transfer rollers 204Y, 204C, 204M, and 204K as the devices for generating the primary transfer electric fields, conductive brush-like devices or non-contact corona chargers, for example, may be employed as the devices for generating the primary transfer electric fields.

The intermediate transfer belt 206 rotates and sequentially passes the primary transfer nips for the Y, C, M, and K colors. Thereby, the Y, C, M, and K toner images are sequentially superimposed and primary-transferred onto the outer circumferential surface of the intermediate transfer belt 206. Accordingly, a superimposed toner image including the superimposed Y, C, M, and K toner images is formed on the outer circumferential surface of the intermediate transfer belt 206 having passed the primary transfer nips.

The secondary transfer roller 208 provided outside the loop of the intermediate transfer belt 206 comes into contact with the outer circumferential surface of the intermediate transfer belt 206 such that the intermediate transfer belt 206 is sandwiched between the secondary transfer roller 208 and the drive roller 201 provided inside the loop. Thereby, a secondary transfer nip is formed. In the vicinity of the secondary transfer nip, the drive roller 201 is grounded. Meanwhile, the secondary transfer roller 208 is applied with a secondary transfer bias opposite in polarity to the toner. In the secondary transfer nip, therefore, a secondary transfer electric field is generated which electrostatically moves the toner from the outer circumferential surface of the intermediate transfer belt 206 toward the secondary transfer roller 208 serving as a secondary transfer member.

The present printer 300 includes a not-illustrated sheet feeding cassette that stores a sheet bundle of a plurality of recording sheets P stacked in the thickness direction. The uppermost recording sheet P of the sheet bundle is fed from the sheet feeding cassette toward a sheet feed path at a predetermined time. The fed recording sheet P is nipped between two rollers of the registration roller pair 250 provided near an end of the sheet feed path. In the registration roller pair 250, the two rollers are driven to rotate to nip a leading end portion of the recording sheet P.

Immediately thereafter, the rotational driving of the two rollers is stopped. Then, the rotational driving of the two rollers is restarted at a time causing the superimposed toner image on the intermediate transfer belt 206 to be superimposed on the recording sheet P in the secondary transfer nip. Due to the action of the above-described secondary transfer electric field, the toner images included in the superimposed toner image on the intermediate transfer belt 206 are secondary-transferred at the same time onto the recording sheet P nipped in the secondary transfer nip, and are formed into a full-color image with the white color of the recording sheet P. In the transfer unit 200, the secondary transfer roller 208 may be replaced by a transfer charger as the device for generating the secondary transfer electric field.

Above the secondary transfer nip, the fixing device 260 is provided which includes a fixing roller 261 including a heat generation source, such as a halogen lamp, and a pressure roller 262. The fixing device 260 brings the fixing roller 261 and the pressure roller 262 into contact with each other to form a fixing nip. The fixing roller 261 and the pressure roller 262 are driven to rotate such that the respective outer circumferential surfaces thereof move in the same direction in the fixing nip. The recording sheet P having passed the secondary transfer nip enters the fixing device 260 and is nipped in the fixing nip. Then, the full-color image is fixed on the recording sheet P with nip pressure and heat applied thereto.

A portion of the outer circumferential surface of the intermediate transfer belt 206 wound around the cleaning backup roller 202 is in contact with an edge of the cantilever-supported cleaning blade 210 of the belt cleaning device 207. Post-transfer residual toner and later-described tone patterns adhering to the outer circumferential surface of the intermediate transfer belt 206 having passed the secondary transfer nip are removed from the outer circumferential surface of the intermediate transfer belt 206 by the cleaning blade 210.

In a print operation using the present printer 300, the image information is first transmitted to the printer 300 by a printer driver of the not-illustrated PC. The printer 300 transmits the image information to the control unit 500 (see FIG. 5) and an image processing unit.

Upon receipt of the image information, the control unit 500 drives not-illustrated drive motors to rotate the intermediate transfer belt 206. At the same time, the photoconductors 101Y, 101C, 101M, and 101K of the respective image forming units 100Y, 100C, 100M, and 100K are driven to rotate. Further, the image processing unit transmits optical writing signals generated on the basis of the image information to the optical writing unit 290. On the basis of the optical writing signals, the optical writing unit 290 generates the writing light Lb for each of the Y, C, M, and K colors, and optically scans the outer circumferential surfaces of the photoconductors 101Y, 101C, 101M, and 101K. Thereby, electrostatic latent images for the Y, C, M, and K colors are formed on the photoconductors 101Y, 101C, 101M, and 101K, and are visualized by the development devices 103Y, 103C, 103M, and 103K. Thereby, Y, C, M, and K toner images are formed on the photoconductors 101Y, 101C, 101M, and 101K. The Y, C, M, and K toner images are superimposed and primary-transferred onto the intermediate transfer belt 206 in the primary transfer nips for the Y, C, M, and K colors to be formed into a superimposed toner image.

Meanwhile, in the not-illustrated sheet feeding cassette, a sheet feed roller is driven to rotate and feeds the recording sheet P. The fed recording sheet P is separated from the other sheets of the sheet bundle by a not-illustrated separation roller, conveyed to the sheet feed path, and nipped by the registration roller pair 250. When the recording sheet P is set not in the sheet feeding cassette but in a not-illustrated manual feed tray, the recording sheet P set in the manual feed tray is fed by a not-illustrated sheet feed roller, separated from the other sheets of the sheet bundle by a not-illustrated separation roller, and conveyed to the registration roller pair 250.

The registration roller pair 250 conveys the recording sheet P toward the secondary transfer nip at a time causing the superimposed toner image formed on the intermediate transfer belt 206 to be superimposed on the recording sheet P. Although it is common to use the grounded registration roller pair 250, the registration roller pair 250 may be applied with a bias to remove paper powder of the recording sheet P.

The toner images included in the superimposed toner image on the intermediate transfer belt 206 are secondary-transferred at the same time onto the recording sheet P conveyed by the registration roller pair 250 and nipped in the secondary transfer nip. Thereafter, the recording sheet P passes the fixing device 260 and is discharged outside the printer 300. If the recording sheet P having a toner image fixed on one surface thereof is to have another image formed on the other surface thereof, the recording sheet P having passed the fixing device 260 is reversed by a not-illustrated switchback device and conveyed to the registration roller pair 250.

Figure 3:
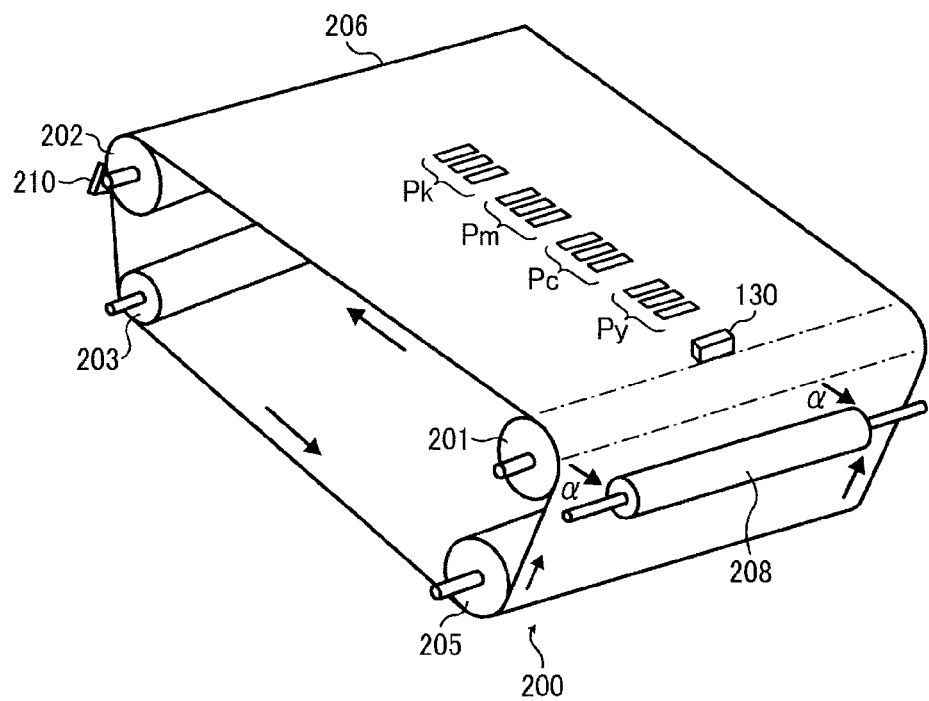
FIG. 3 is a perspective view illustrating a transfer unit of the printer.

FIG. 3 is a perspective view illustrating transfer unit 200. The image forming unit 100 form not only the toner image based on the image information sent from an external device such as PC but also gradation patterns (potential-control toner patterns) on the surface of the intermediate transfer belt 206 at a predetermined timing. The gradation patterns have yellow gradation pattern portion Py, cyan gradation pattern portion Pc, magenta gradation pattern portion Pm, and black gradation pattern portion Pk, which are formed when the toner amount estimation process is executed. The gradation pattern, serving as the potential-control toner pattern, is used for controlling potential of the voltages (e.g., a charging bias, a development bias, transfer bias, operation of an exposure device) in the image forming unit 100 and the potential of the transfer bias.

The gradation pattern portions Py, Pc, Pm, and Pk have multiple test toner images formed under different conditions of toner adhesion quantity per area (hereinafter just "toner adhesion quantity"). When the gradation pattern images (hereinafter just "patterns") are formed, the secondary transfer roller 208 is moved in a direction indicated by arrow A by a contact-separation mechanism (not shown) and then separated from the intermediate transfer belt 206. Therefore, the gradation patterns pass a facing portion facing the secondary transfer roller 208 without moving to the surface of the secondary transfer roller 208.

It is to be noted that, in the present embodiment, each of the gradation pattern portions Py, Pc, Pm, and Pk has three test toner images whose toner adhesion quantities are different respectively. However, it is to be noted that each of the gradation pattern portions Py, Pc, Pm, and Pk may have more than three test toner images of toner different adhesion quantities.

In entire area of the circumferential direction of the intermediate transfer belt 206, in a portion in which the drive roller 201 contacts an area downstream from the area facing the secondary transfer roller 208 in which the surface of intermediate transfer belt 206 moves, a reflection-type optical sensor unit 130 is disposed facing the outer surface of the intermediate transfer belt 206. When the test toner images in the gradation patterns pass directly under the reflection-type optical sensor unit 130, the reflection-type optical sensor unit 130 receives the reflection light whose amount depends on the toner adhesion quantity of the test toner images.

Figure 4:
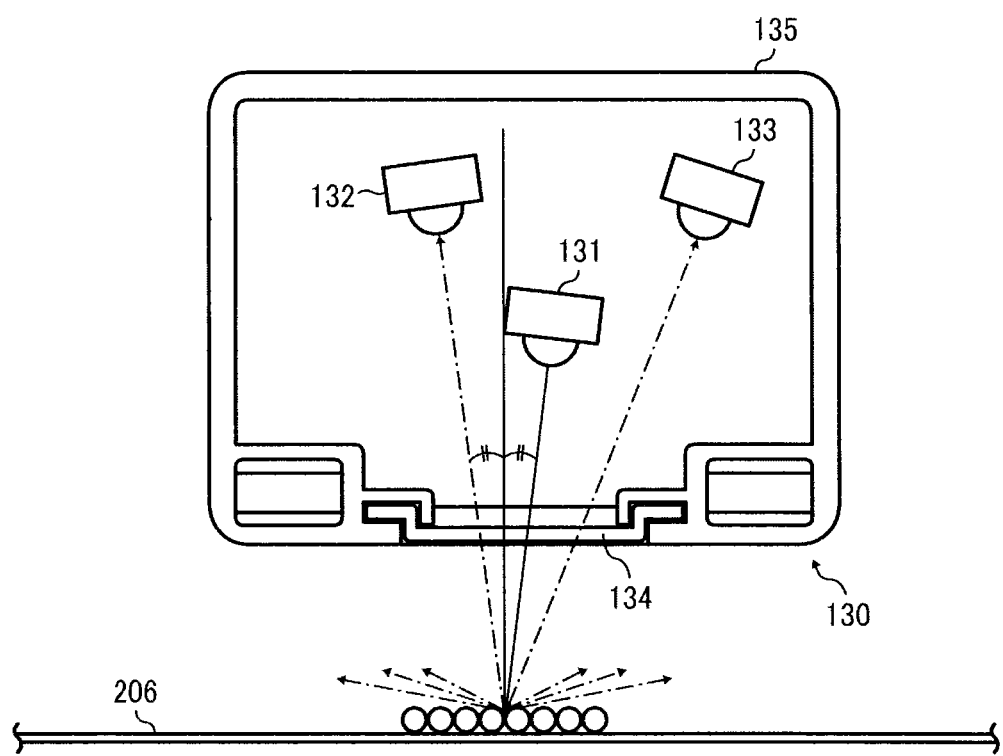
FIG. 4 is an enlarged configuration diagram illustrating a reflection-type optical sensor unit.

FIG. 4 is an enlarged configuration diagram illustrating the reflection-type optical sensor unit 130. In FIG. 4, the reflection-type optical sensor unit 130 includes an LED 131 serving as a light emitting device, a regular reflection light receiving element 132, a diffuse reflection light receiving element 133, a glass cap 134, and a casing 135. The LED 131 may be replaced by, for example, a laser light emitting device as the light emitting device. Although in the present embodiment a phototransistor is used for each of the regular reflection light receiving element 132 and the diffuse reflection light receiving element 133, alternatively a photodiode and an amplifier circuit may be used, for example.

Infrared light emitted from the LED 131 passes through the condenser lens 134 and reaches the test toner image formed on the intermediate transfer belt 206. Then, a portion of the infrared light that is regularly reflected on a surface of the test toner image to be converted into regular reflection light passes through the condenser lens 134 again, and is received by the regular reflection light receiving element 132. The regular reflection light receiving element 132 outputs a voltage corresponding to the amount of received light. The output value from the regular reflection light receiving element 132 is converted into digital data by an A/D converter 501 (see FIG. 5) and input to the control unit 500. Another portion of the infrared light that is diffusedly reflected on the surface of the test toner image to be converted into diffuse reflection light passes through the condenser lens 134 again, and is received by the diffuse reflection light receiving element 133. The diffuse reflection light receiving element 133 outputs a voltage corresponding to the amount of received light. The output value is converted into digital data by the A/D converter 501 and input to the control unit 500.

The regular reflection light receiving element 132 is disposed inside a dedicated tube and is independent from the LED 131 and the diffuse reflection light receiving element 133. Opening of the tube is directed to a direction in which the regular reflection light is received. The diffuse reflection light receiving element 133 is also disposed inside a dedicated tube and is independent from the LED 131 and the regular reflection light receiving element 132. Opening of the tube is directed to a direction in which the diffuse reflection light is received. With this configuration, the receiving directivity of regular reflection light and diffuse reflection light can be improved.

Figure 5:
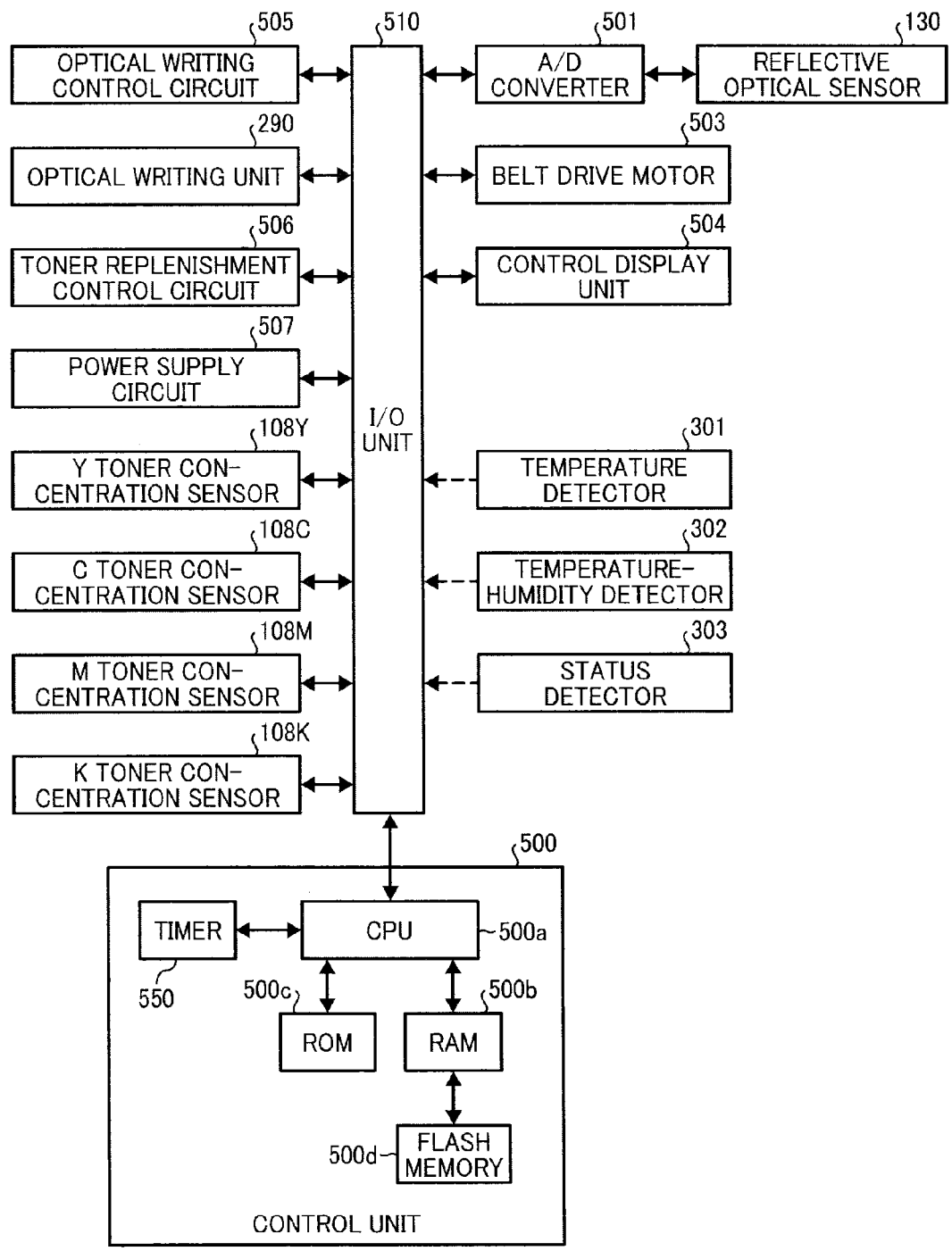
FIG. 5 is a block diagram illustrating a portion of an electrical circuit of the printer.

FIG. 5 is a block diagram illustrating a portion of an electrical circuit of the printer 300 according to the embodiment. As illustrated in FIG. 5, the control unit (processor) 500 includes a central processing unit (CPU). In FIG. 5, the control unit 500 serving as an imaging condition adjustment device includes a central processing unit (CPU) 500a, a random access memory (RAM) 500b for temporarily storing a variety of data, a read-only memory (ROM) 500c for storing a control program and a variety of data, and a flash memory 500d for storing a variety of data in a nonvolatile manner. The control unit 500 is connected to a variety of peripheral devices via an input-output (I/O) unit 510 that relays signal transmission and reception between the control unit 500 and the peripheral devices. Although the control unit 500 is connected to the variety of peripheral devices via the I/O unit 510, FIG. 5 illustrates only major ones of the peripheral devices. An optical writing control unit 505 controls the driving of the optical writing unit 290.

A toner replenishment control circuit 506 controls the driving of the not-illustrated toner replenishing devices which individually replenish the development devices 103Y, 103C, 103M, and 103K for the Y, C, M, and K colors with the respective toners in the toner bottles 90Y, 90C, 90M, and 90K for the respective colors. Power supply circuits 507 output, for example, the above-described biases including the primary transfer bias for the respective colors, the secondary transfer bias, and the development bias to be applied to the development sleeve 109 included in each of the development devices 103Y, 103C, 103M, and 103K for the respective colors. Each of the Y, C, M, and K toner concentration sensors 108Y, 108C, 108M, and 108K measures the toner concentration of the developer in the corresponding one of the development devices 103Y, 103C, 103M, and 103K for the respective colors. The A/D converter 501 converts the value of the voltage output from the reflection-type optical sensor unit 130 into digital data.

A belt-driving motor 503 is a driving source to drive the drive roller 201. An operational display 504 includes an image display to display image and various keys to which the user inputs input-information. The printer 300 may further include a temperature detector 301 or a temperature-humidity detector 302, and a status detector 303.

The optical writing control circuit 505 controls the driving of the optical writing unit 290 on the basis of a control signal input from the control unit 500 via the I/O unit 510. The power supply circuits 507 control the output values of the biases to be output therefrom, on the basis of control signals input from the control unit 500 via the I/O unit 510.

The control unit 500 performs the following toner amount estimation process at a predetermined time, such as every time a predetermined time elapses and every time a predetermined number of sheets are printed.

Figure 6:
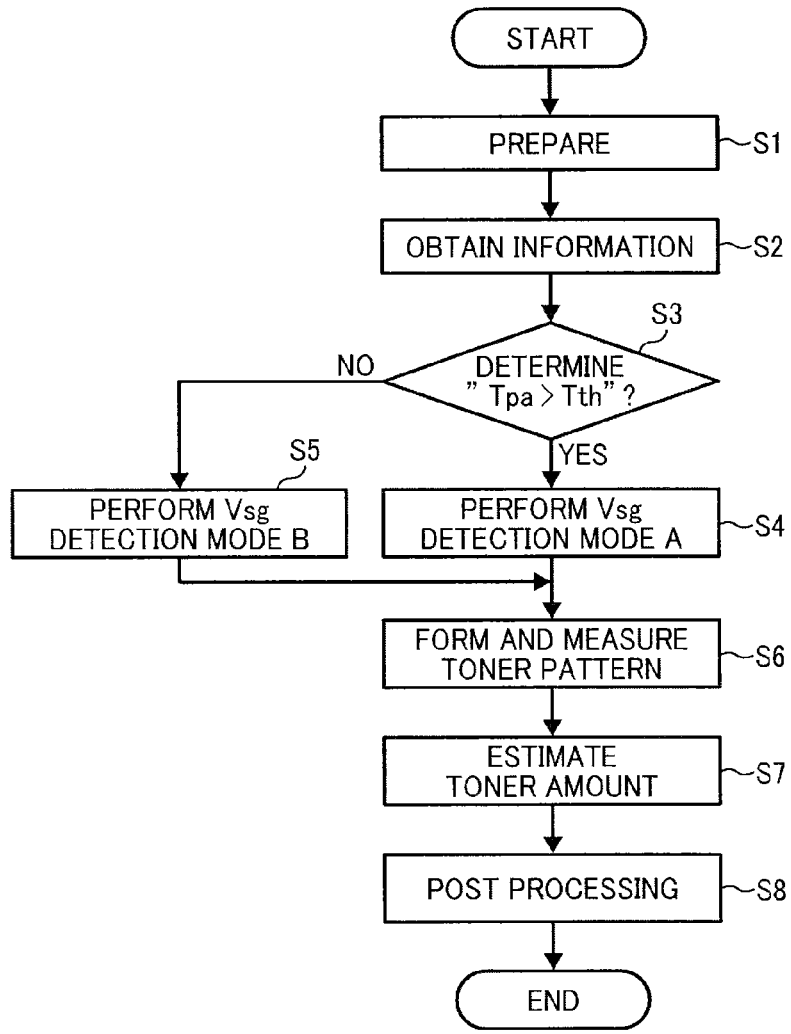
FIG. 6 is a flow chart illustrating a toner amount estimation process executed in a control unit in the printer.

FIG. 6 is a flow chart illustrating the toner amount estimation process executed in the control unit 500 in the printer 300. Initially, as a preparation process at step S1, similarly to the print operation described above, the photoreceptor 101 and the intermediate transfer belt 206 are rotated, timed to coincide with the start rotation, the charge bias from the charger 102 is applied to the photoreceptor 101, and the development bias is applied to the development sleeve. What is different from the print operation is that the secondary transfer roller 208 is separated from the intermediate transfer belt 206 so as not to transfer the gradation patterns containing the test toner images onto the print target (e.g., recording sheet P). Therefore, if the secondary transfer roller 208 contacts the intermediate transfer belt 206 before preparation, the secondary transfer roller 208 is being separated at this step S1.

Then, as information acquiring process at step S2, an elapsed time from stop of the intermediate transfer belt 206 to the present time is obtained. More specifically, as illustrated in FIG. 5, the control unit 500 in the printer 300 includes a timer 550. When the intermediate transfer belt 206 stops driving, the control unit 500 obtains the stopped timing from the timer 550 and stores it in the non-volatile memory 500d. Subsequently, when the toner amount estimation process is started, the control unit 500 obtains the start timing from the timer 550, and calculates the difference between the start timing and the stopped timing stored in the flash memory 500d when the intermediate transfer belt 206 stops and sets the calculated difference as an elapsed time Tpa.

Then, as the determination process at step S3, the control unit 500 compares the elapsed time Tpa with a predetermined threshold time Tth. When the elapsed time Tpa is longer than the predetermined threshold time Tth (Yes at step S3), the control unit 500 executes "Vsg detection mode A" at step S4. Conversely, when the elapsed time Tpa is equal to or shorter than the predetermined threshold time Tth (No at step S3), the control unit 500 executes "Vsg detection mode B" at step S5.

Herein, "Vsg" is the voltage of a surface sensor output corresponding to the amount of light reflected from a clear background surface (hereinafter just "surface") of the intermediate transfer belt 206 when the reflection-type optical sensor unit 130 directs light onto the surface of the intermediate transfer belt 206.

By contrast, "Vsp" is the voltage of a toner-pattern output corresponding to the amount of light reflected from the gradation patterns when the reflection-type optical sensor unit 130 directs light onto the gradation patterns containing the multiple test toner images.

"Vsg detection mode A" is the detection mode to calculate a first-surface sensor output Vsg1 as the surface sensor output in a same position of one previous cycle at the position at which the gradation patterns are formed on the intermediate transfer belt 206.

Conversely, the Vsg detection mode B is the mode during which the first-sensor output Vsg1 is not detected, and instead of the first-surface sensor output Vsg1, calculates the second-surface sensor output Vsg2 of the surface sensor output Vsg at the area immediately in front of the gradation pattern.

Figure 7:
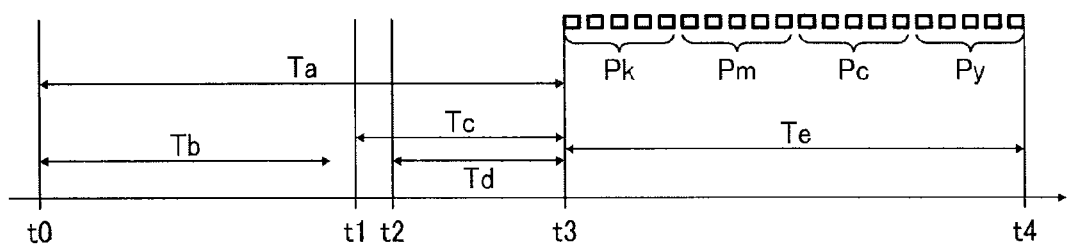
FIG. 7 is an explanatory chart illustrating reading process in the reflection-type optical sensor unit.

FIG. 7 is a timing chart illustrating a reading (detecting) process in the reflection-type optical sensor unit 130. In FIG. 7, "t0" is a start timing at which the reflection-type optical sensor unit 130 reads N numbers of first-sensor outputs Vsg1 from first surfaces of the intermediate transfer belt 206, and "t1" is a start timing at which the reflection-type optical sensor unit 130 writes (forms) the gradation patterns. "t2" is a start timing at which the reflection-type optical sensor unit 130 reads an average value "Vsg2avg" of the multiple second-surface sensor outputs Vsg2 from a second surface of the intermediate transfer belt 206. "t3" is a start timing at which the reflection-type optical sensor unit 130 reads the gradation patterns, and "t4" is a finish timing to read the gradation patterns.

In FIG. 7, a time period from the time "t0" to the time "t3" corresponds to a 1-cycle surface movement time Ta during which the intermediate transfer belt 206 is rotated one revolution. The surface movement time Ta is obtained by dividing a length Np of the intermediate transfer belt 206 by a surface movement velocity Vp of the intermediate transfer belt 206 (Ta=Lp/Vp).

A time period from "t0" to "t1" corresponds to a first surface reading time period Tb during which N numbers of first-sensor outputs Vsg1(n) are read. A time period from "t1" to "t3" corresponds to a toner-pattern writing-reading time period Tc from the writing start timing at which the gradation patterns are written to the start time at which the gradation patterns are read. A time period from "t2" to "t3" corresponds to a second-surface reading time period Td during which the second-surface output average Vsg2avg is read. A time period from "t3" to "t4" corresponding to is a pattern surface movement time period Te, during which the surface of the intermediate transfer belt 206 is traveled for lengths of the gradation patterns, obtained upon dividing a length Le of formation regions of the gradation patterns by the surface movement velocity Vp (Te=Le/Vp).

The predetermined threshold time Tth used in the determination process at step S3 is decided in advance, based on the hardness and material of the intermediate transfer belt 206, curl characteristics of the intermediate transfer belt 206 caused by tension of the tension rollers exerted against the intermediate transfer belt 206, and reflection characteristics of the reflection-type optical sensor unit 130. If the standby time (idle time) is long, as illustrated in FIG. 2, the intermediate transfer belt 206, wound around the multiple tension rollers 201, 202, 203, and 205, partially curves around outer circumferential surfaces of the tension rollers 201, 202, 203 and 205.

Once the intermediate transfer belt 206 partially curls, the reflection characteristics of the intermediate transfer belt 206 change. Therefore, when the toner amount is estimated, it is preferable that the surface sensor output Vsg detected in a portion (first time-surface) identical to the portion in which the gradation patterns are formed. Accordingly, when the standby time is long, the control unit 500 executes the Vsg detection mode A.

The toner pattern writing and reading process at step S6 when the Vsg detection mode A is executed at step S4 is described. When the Vsg detection mode A is executed, the reflection-type optical sensor unit 130 detects the first-surface sensor output Vsg1, forms the gradation patterns based on the first-surface sensor output Vsg1, and then detects the toner-pattern sensor output Vsp from the gradation patterns.

In preliminary preparation, the LED 131 in the reflection-type optical sensor unit 130 emits light. When the light amount of the LED 131 is turned on after a sufficient time has elapsed from the timing when the LED 131 is turned off, due to the heat characteristics of the elements of the LED 131, there is a certain time lag from a start timing to emit light to a stabilization timing at which the light emission amount is stabilized.

The time lag depends on the characteristic of the LED 131, normally; the time lag is 2 seconds. Accordingly, after at least two seconds has elapsed from the timing at which the LED 131 of the reflection-type optical sensor unit 130 is turned on, and after the light emission amount of the LED 131 is stabilized, the control unit 500 starts detecting the first-surface sensor output Vsg1. With this operation, the occurrence of the detection error caused by the unstable light emission amount of the LED 131 can be avoided.

A time period during which the reflection-type optical sensor unit 130 detects the gradation patterns or the first time-surface in the Vsg detection mode A corresponds to the 1-cycle surface movement time Ta during which the intermediate transfer belt 206 is rotated one revolution. The surface movement time Ta is obtained by adding quotient obtained by dividing the length Le of the intermediate transfer belt 206 by the surface movement velocity Vp of the intermediate transfer belt 206 to the pattern surface movement time Te obtained by dividing the length Le of formation regions of the gradation patterns by the surface movement velocity Vp. In other words, Ta=(Lp/Vp)+Te(=Le/Vp).

At the timing t0, the reflection-type optical sensor unit 130 starts reading the amount of reflection light as the first-surface sensor output Vsg1. Sampling rate is decided by the surface movement velocity Vp of the intermediate transfer belt 206 and the throughput of the CPU 500a, which is approximately 1-4 (msec/sampling)

At the timing t1 at which writing the gradation patterns is started, the latent-image gradation patterns is written on the photoreceptor 101. Then, the latent-image gradation patterns on the photoreceptor 101 are developed to form the toner image gradation patterns, and the toner gradation patterns are transferred on the transfer belt 206. At the pattern reading start timing t3, front ends of the gradation patterns transferred onto the intermediate transfer belt 206 reach the detection range of the reflection-type optical sensor unit 130, and the reflection-type optical sensor unit 130 starts reading the gradation patterns.

The toner-pattern sensor output Vsp(n) as the detection values obtained upon reading the gradation patterns are stored in the flash memory once and are subjected to the data processing. As the first-surface sensor output Vsg1 of the sensor output Vsg detected at the position identical to the gradation patterns, the control unit 500 acquires the N average values of the first-surface sensor output Vsg1avd (n) (m: number of the gradient patterns) based on the data of the surface sensor output Vsg in the portion (first time-surface) to be formed the gradation patterns calculated in advance based on the timing of arriving the gradation patterns at the detection range of the reflection-type optical sensor unit 130.

Next, the toner amount estimation process when the Vsg detection mode A is executed at step S7 is described. When the Vsg detection mode A is executed, the control unit 500 corrects the toner-pattern sensor output Vsp read from the gradation patterns, using the average value of the first-surface sensor output Vsg1avg as the surface sensor output Vsg before of the intermediate transfer belt 206 is rotated one cycle. The correction is calculated as follows.

$$Vspavgnew(m) = Vspavg(m) \times Vsg1avg(m)/Vsgtgt \qquad (1)$$

Vspavgnew (m): corrected value for the average of the m-th gradation pattern read.

Vspavg(m): m-th gradation pattern read data average.

Vsg1ave(m): average of N numbers of first-surface sensor output Vsg1 from a portion (first time-surface) whose width is identical to the portion in which the m-th gradation pattern will be formed, one cycle before the intermediate transfer belt 206 is rotated.

Vsgtgt: ideal value of the surface sensor output Vsg.

As alternative correction method, all the respective gradation patterns are corrected from front to end by all the first-surface sensor outputs Vsg1 of the surface sensor output Vsg that is one cycle before the intermediate transfer belt 206 is rotated.

This corrected value is calculated by the following formula 2.

$$Vspnew(k) = Vsp(k) \times Vsg1(k)/Vsgtgt \qquad (2)$$

Vspnew (k): corrected value for the k-th gradation pattern read from the beginning.

Vsp(k): k-th gradation pattern read data from the beginning.

Vsg1($k$): the first-surface sensor output Vsg1 detected from a portion (first time-surface) identical to the gradation patterns whose width is identical to the portion in which the k-th gradation pattern will be formed, one cycle before the intermediate transfer belt 206 is rotated.

Vsgtgt: ideal value of the surface sensor output Vsg.

Like that shown the formula 2, the correction of the data based on the formula 1 is unnecessary when each of the data is corrected using the first-surface sensor outputs Vsg1 as the surface sensor output Vsg one cycle before the intermediate transfer belt 206 per read one data.

Meanwhile, the toner gradation pattern formation process and detection process at step S6 when the Vsg detection mode B is executed is described. The Vsg detection mode B is the mode during which the first-surface sensor output Vsg1 as the surface sensor output Vsg, redetected in the portion (first time-surface) identical to the portion one cycle before the intermediate transfer belt 206, is not detected. In addition, when the Vsg detection mode B is executed, the control is started from the time t1 (see FIG. 7) at which the gradation patterns are written. Similarly to the Vsg detection mode A, it is necessary to start detecting the surface sensor output Vsg after the light emission amount of the LED 131 is stabilized in the Vsg detection mode B. However, since only stabilizing the light emission amount have to be finished by the Vsg2avg gradation pattern start reading timing, the gradation pattern writing start timing t1 can be set before the timing at which the light emission amount of the LED 131 is stabilized.

A detection time period during which the reflection-type optical sensor unit 130 detects the gradation patterns and a surface (second time-surface) in the Vsg detection mode B is obtained by adding the Vsg2avg reading time period Td and the pattern surface movement time Te obtained by dividing the length of the gradation patterns Le by the surface movement velocity of the intermediate transfer belt Vp. In other words, T=Td+Te(Te=Le/Vp).

In the Vsg detection mode B, at the gradation pattern start timing t1, the latent-image gradation patterns are written on the photoreceptor 101. Then, the latent-image gradation patterns on the photoreceptor 101 are developed to the toner-image gradation patterns, and the toner gradation patterns are transferred onto the transfer belt 206. At the pattern reading start timing t3, the front ends of the gradation patterns on the intermediate transfer belt 206 reaches the detection range of the reflection-type optical sensor unit 130 and the reflection-type optical sensor unit 130 starts reading the gradation patterns At the Vsg2avg start timing t2 between the gradation pattern writing start timing t1 and the gradation pattern reading start timing t3, the reflection-type optical sensor unit 130 start reading the amount of light reflected from the second ground surface as the second-surface sensor output Vsg2. Then, by the gradation pattern reading start timing t3, the reflection-type optical sensor unit 130 finishes reading a predetermined number (q) of the amount of reflection light detected from q numbers of detection regions as the second-surface sensor output Vsg2. After which, the average value Vsg2ave of the q numbers of second-surface sensor output Vsg2 is obtained.

Next, the toner amount estimation process when the Vsg detection mode B is executed at step S7 is described. When the Vsg detection node is executed, the toner-pattern sensor outputs Vsp read in the gradation patterns are corrected, using the second-surface sensor output Vsg2 detected in a portion (second time-surface) at the area immediately in front of the gradation patterns.

This corrected value is calculated as follows.

$$Vspavgnew(r) = Vspavg(r) \times Vsa2avg(r)/Vsgtgt \qquad (3)$$

Vspavegnew (r): corrected value for the average of the r-th gradation pattern.

Vspavg (r): r-th gradation pattern read data average.

Vsg2avg (r): average of the q-th second surface sensor output Vsg2($q$) detected from the area immediately in front of the r-th gradation pattern.

Vsgtgt: ideal value of the surface sensor output Vsg.

Then, as a post-processing at step S8, based on the corrected value calculated by the formula 3, the control unit 500 calculates the respective estimate values of the toner adhesion quantity of the respective test toner-image gradation patterns, using the relation between the reading value set in advance and the toner adhesion quantity of the gradation patterns. Then, based on the calculation result, the control unit 500 adjust the imaging condition so that respective colors of toner images Y, C, M, and K can implement the target toner adhesion quantities. As for adjusting the imaging condition, a method in which a charging voltage to uniformly charge the photoreceptor and development bias is adjusted is proposed in, for example, JP-H09-211911-A. Alternatively, the toner concentration of the developer may be adjusted. In the printer 300 of the present disclosure, obtained toner adhesion quantity is used for the control so that the image density can be kept constant. In addition, this example of the control method can be applied to correct the color deviation based on the estimation of a distance among the respective toner lines.

As described above, the image forming apparatus 300 of the present disclosure includes the image bearing member (intermediate transfer belt) 206, the image forming unit 100, the reflection light detectors 130, and the controller (control unit) 500. The image bearing member 206 moves endlessly and has a surface to bear a toner image and a potential-control toner pattern (gradation pattern). The image forming unit 100 forms the toner image and the potential-control toner pattern onto the surface of the image bearing member 206. The reflection light detectors 130 has a light source 131 to emit light onto the surface image bearing member 206 and the potential-control toner pattern formed on the image bearing member 206 and light receiving elements 132 and 133 to detect the amount of light reflected from the potential-control toner pattern formed on the surface of the image bearing member as toner attraction output, and the amount of light reflected from the surface of the image bearing member 206 as a surface output. The controller 500 detects toner information of the toner image based on the toner attraction output corresponding to the detected amount of light reflected from the potential-control toner pattern formed on the image bearing member 206, and the surface output corresponding to the amount of light reflected from the surface of the image bearing member 206. The controller 500 controls the toner image forming unit 100 based on the detected toner information. The surface output contains a first surface output (first-surface sensor output Vsg1) and a second surface output (second-surface sensor output Vsg2). The first surface output Vsg1 is detected from the first time-surface of the image bearing member 206 positioned identical to the potential-control toner pattern. The first time-surface is positioned an integer multiple of revolutions upstream from the potential-control toner pattern in a surface movement direction in which the surface of the image bearing member 206 is moved, or an integer multiple of revolutions downstream from the potential-control toner pattern in the surface movement direction. The second surface output Vsg2 is detected from the second time-surface of the image bearing member 206 positioned different from the potential-control toner pattern. The second time-surface is positioned at a location shorter than one revolution upstream or downstream from the potential-control toner pattern in the surface movement direction. The controller 500 determines whether to execute a first-surface output control <Vsg detection mode A> during which the reflection light detector 130 detects at least the first time-surface of the image bearing member 206, or a second-surface output control <Vsg detection mode B> during which the reflection light detector 130 detects only the second time-surface of the image bearing member 206 based on use condition of the image forming apparatus 300.

With this configuration, as described above, the detection accuracy can be improved and lengthening the downtime caused by the image density adjustment can be minimized. It is to be noted that, in above-described embodiment, in the Vsg detection mode A, only the first-surface sensor output Vsg1 is reflected to the correction. However, in the Vsg detection mode A, both the first-surface sensor output Vsg1 and the second-surface sensor output Vsg are reflected.

Herein, a reason why the surface sensor output Vsg detected by the surface of the intermediate transfer belt 206 fluctuates is described below. The surface sensor output Vsg fluctuates because there is a deviation of glossiness in fabrication of the belt surface of the intermediate transfer belt 206. A material used for the intermediate transfer member of an endless belt is required to have smaller elastic to replicate the image patterns. In addition, the material of the belt is required to have flame retardant, strength, and electric stability, in order to satisfy these conditions, heat resistant resin such as polyimide is used as base material.

Although, according to the heat resistant resin such as polyimide resin, when the smooth film is formed, the firm itself can obtain the sufficient high reflection-light glossiness having over 100. In order to obtain separation ability as the intermediate transfer member, if a separation layer is formed on the surface, generally, the separation layer is thin, orientation order lacks of organization, and the glossiness is not even.

The sensor output Vsg caused by the deviation of the glossiness of the fabrication of the belt surface is partially changed, similar to the Vsg detection mode A, detecting the first-sensor output Vsg1 is required. However, the surface is detected when the intermediate transfer belt 206 is installed in the printer 300, and then is corrected so that the influence of the fluctuation is reflected. The influence caused by the deviation of the glossiness is not need to be considered whenever the toner information is detected.

The surface sensor output Vsg fluctuates because of the scratch and stein of the intermediate transfer belt 206 when the intermediate transfer belt 206 is used. The surface of the intermediate transfer belt 206 contacts the cleaning blade 210 in the cleaning device 200 to remove the transfer-residual toner and the secondary transfer rollers 208 serving as the facing roller to transfer the toner image onto the recording sheet P. Due to the sliding friction with these other members, the surface layer of the intermediate transfer belt is scratched, which makes the glossiness unevenness. In addition, the extraneous is extended on the surface of the intermediate transfer belt 206 and becomes the stain that cannot be removed by the belt-cleaning device 207, which becomes the glossiness uneven.

Since the surface sensor output Vsg caused by the scratch and stein in use may be affected in short time, it is preferable that these influence be considered every time the toner adhesion quantity estimation operation is executed.

However, the scratch and grime in use is generated within a certain wide range in the surface movement direction, and theses abnormal states can be detected using the second time-surface positioned different from the gradation pattern forming portions and the detection result is reflected to the correction. Accordingly, only by calculating the second-surface sensor output Vsg2 immediately in front of the gradation pattern formation region, the toner amount can be appropriately estimated, like that flow of the Vsg detection mode B.

When the Vsg detection mode B is used, it becomes unnecessary to rotate the intermediate transfer belt 206 at least one revolution before the gradation patterns are formed, downtime is not lengthened even when the reflection light is detected and the detection result is fed back to the correction every time the toner adhesion quantity is estimated.

The surface sensor output Vsg is disturbed due to the curl characteristics of the intermediate transfer belt 206. In order to keep blade-cleaning ability, high glossiness, and the separation ability from the recording sheet P, the intermediate transfer belt 206 is required to have a certain degree of hardness.

However, tension strength from the multiple tension rollers 201, 202, 203, and 205 is exerted to the intermediate transfer belt 206, and the tension strength acts on the intermediate transfer belt 206 while the intermediate transfer belt 206 is at rest. Therefore, when the intermediate transfer belt 206 is left for a long time without moving the surface thereof, the intermediate transfer belt 206 is curled around the portions where the tension rollers support. Diffusion light reflected from the detection region on the surface of the curled intermediate transfer belt 206 incidents in random to the regular reflection light receiving element 132 of the reflection-type optical sensor unit 130, and the surface sensor output Vsg fluctuates.

The fluctuation in the surface sensor output Vsg caused by the curled surface is partially generated, and therefore, detecting the first-surface sensor output Vsg1 like that the Vsg detection mode A is required.

However, the intermediate transfer belt 206 is curled when the intermediate transfer belt 206 is left for a long time without moving the surface thereof. The data of the toner amount estimation needs to be corrected so that the influence of the fluctuation is fed back to the data only when the intermediate transfer belt 206 is left over a predetermined time, and it is not necessary to be considered every time the toner information is detected.

As described above, in the printer 300, the control unit 500 controls the imaging condition so that the fluctuation in the surface sensor output Vsg is detected based on the trigger to fluctuate the surface sensor output Vsg and use condition based on the trigger in the printer 300, which can prevent the downtime from lengthening and estimate the toner adhesion quantity appropriately.

In order to obtain better result to solve fluctuation caused by the curl characteristics, as one configuration, the image forming apparatus 300 includes a stop-time detector (timer) 550) to measure stop time of the image forming apparatus 300. The controller 500 executes the first-surface output control <Vsg detection mode A> when the measured stop time is longer than a predetermined value and executes the second-surface output control <Vsg detection mode B> when the measured stop time is equal to or shorter than a predetermined value.

With this setting, only when the stop time (left time, idle time) is long, the control unit 500 determines whether to execute or not the first-surface output control that the reflection light detectors 130 detects the first time-surface positioned an integer multiple of revolutions upstream or downstream from the gradation pattern in the surface movement direction. Thus, lengthening the downtime caused by the image density adjustment can be minimized.

As described above, since executing the Vsg detection mode A is required for long time, it is necessary to decrease the fluency of executing the Vsg detection mode A when possible.

In addition, the intermediate transfer belt 206 is likely to curl under high temperature and high humidity conditions and when the left time of the printer 300 is long. As the information is greater, the fluency of the detection can be optimized. If the obtained information is only one, the fluency in the execution of the executing the Vsg detection mode A can be reduced. One example of threshold values is illustrated in FIGS. 8A and 8B. In FIGS. 8A and 8B, humidity is 25 [° C.], absolute humidity is 15 [g/m$^3$], Left time is 6 [Hour].

The "absolute humidity" represents the relation with saturation water vapor pressure, which is different from relative humidity [% RH] commonly used; more specifically, the "absolute humidity" is the value indicating the amount of moisture per its value. The absolute humidity is determined by the relative humidity and the temperature. FIGS. 8A and 8B are one example of calculation table to acquire the absolute humidity.

As one example for requiring the absolute humidity using the FIGS. 8A and 8B, when the temperature is 20 [° C.] and relative humidity is 65 [% RH], the absolute humidity is 14.99 [g/m$^3$]. Herein, the absolute humidity is not limited as judgment of use condition, but the relative humidity can be adopted as judgment of use condition in the printer 300.

As the use condition of the printer 300, the image forming apparatus 300 further includes a temperature detector 301 measures ambient temperature inside or near the image forming apparatus 300. The control unit 500 executes the first-surface output control <Vsg detection mode A> when the measured ambient temperature is higher than a predetermined value, and executes the second-surface output control <Vsg detection mode B> when the measured ambient temperature is equal to or lower than a predetermined value.

With this setting, only when the measured ambient temperature is high, the control unit 500 determines whether to execute or not the first-surface output control that the reflection light detectors 130 detects the first time-surface positioned an integer multiple of revolutions upstream or downstream from the gradation pattern in the surface movement direction. Thus, lengthening the downtime caused by the image density adjustment can be minimized.

As another use condition of the printer 300, the image forming apparatus further includes a temperature and humidity detector 302 to measure ambient temperature and ambient humidity inside or near the image forming apparatus 300. The control unit 500 executes the first-surface output control <Vsg detection mode A> when the measured ambient temperature is higher than a predetermined value and the measured ambient humidity is higher than a predetermined value, ands executes the second-surface output control under the condition other than when both the measured ambient temperature and ambient humidity are higher than a predetermined value.

With this setting, only when both the measured ambient temperature and measured humidity are high, the control unit 500 determines whether to execute or not the first-surface output control that the reflection light detectors 130 detects the first time-surface positioned an integer multiple of revolutions upstream or downstream from the gradation pattern in the surface movement direction. Thus, lengthening the downtime caused by the image density adjustment can be minimized.

As a combination configuration, the image forming apparatus further includes a stop-time detector (timer) 550 to measure stop time of the image forming apparatus 300 and the temperature detector 301 to measure ambient temperature inside or near the image forming apparatus 300. The control unit 500 executes the first-surface output control when the measured stop time is longer than a predetermined value and the measured ambient temperature is higher than a predetermined value, and executes the second-surface output control under the condition other than when both the measure stop time and the measured ambient temperature are higher than the respective predetermined values.

With this setting, only when n the measured stop time is long and the measured ambient temperature is high, the control unit 500 determines whether to execute or not the first-surface output control that the reflection light detectors 130 detects the first time-surface positioned an integer multiple of revolutions upstream or downstream from the gradation pattern in the surface movement direction. Thus, lengthening the downtime caused by the image density adjustment can be minimized.

As another combination variation, the image forming apparatus 300 further includes a stop-time detector (timer) 550 to measure stop time of the image forming apparatus; and a temperature and humidity detector 302 to measure ambient temperature and ambient humidity inside or near the image forming apparatus 300. The control unit 500 executes the first-surface output control when the measured stop time is longer than a predetermined value, the measured ambient temperature is higher than a predetermined value, and the measured ambient humidity is higher than a predetermined value, and executes the second-surface output control under the condition other than when all the measure stop-time, the measured ambient temperature, and the ambient humidity are higher than the respective predetermined values.

With this setting, only when the measured stop time is long and the measured ambient temperature and measure absolute humidity are high, the control unit 500 determines whether to execute or not the first-surface output control that the reflection light detectors 130 detects the first time-surface positioned an integer multiple of revolutions upstream or downstream from the gradation pattern in the surface movement direction. Thus, lengthening the downtime caused by the image density adjustment can be minimized.

In another use condition, in order to reduce the frequency in executing the Vsg detection mode A as much as possible, when expendables, such as, the image forming unit 100 housed in the process cartridge, the toner bottle 90, and the intermediate transfer belt 60 are replaced, and the control unit 500 (status detector 303) detects these replacement operation, the control unit 500 determines whether the Vsg detection mode A and the Vsg detection mode B is executed only when the replacement is detected. Alternatively, when the printer 300 is not in the replacement status, the control unit 500 executes the Vsg detection mode B.

More specifically, the image forming apparatus 300 further includes a status detector to detect that expendable (e.g., the image bearing member 206, toner container 90) is exchanged. The control unit 500 determines whether the first-surface output control or the second ground-surface output control mode is executed only when the exchange detector detects that the expendable is exchanged, and executes the second-surface output control other than when the status detector detects that the expendable is exchanged.

With this setting, only when the status detector 303 detects that the expendable (e.g., transfer belt 206, toner container 90, or recording sheet P) is replaced, the control unit 500 determines whether to execute or not the first-surface output control that the reflection light detectors 130 detects the first time-surface positioned an integer multiple of revolutions upstream or downstream from the gradation pattern in the surface movement direction. Thus, lengthening the downtime caused by the image density adjustment can be minimized.

Numerous additional modifications and variations are possible in light of the above teachings. It is therefore to be understood that within the scope of the appended claims, the disclosure of this patent specification may be practiced otherwise than as specifically described herein.

What is claimed is:

1. An image forming apparatus comprising:
   an endless rotary image bearing member having a surface to bear a toner image and a potential-control toner pattern;
   an image forming unit to form the toner image and the potential-control toner pattern onto the surface of the image bearing member;
   a reflection light detector having a light source to emit light onto the surface of the image bearing member and the potential-control toner pattern formed on the image bearing member and a light-receiving element to detect the amount of light reflected from the potential-control toner pattern formed on the surface of the image bearing member as a toner attraction output, and the amount of light reflected from the surface of the image bearing member as a surface output; and
   a controller to detect toner information of the toner image based on the toner attraction output corresponding to the detected amount of light reflected from the potential-control toner pattern formed on the image bearing member, and the surface output corresponding to the amount of light reflected from the image bearing member, the controller controlling the image forming unit based on the detected toner information,
   wherein the surface output comprises:
      a first surface output detected from a first time-surface of the image bearing member positioned identical to the potential-control toner pattern, the first time-surface positioned one of an integer multiple of revolutions upstream from the potential-control toner pattern in a surface movement direction in which the surface of the image bearing member is moved and an integer multiple of revolutions downstream from the potential-control toner pattern in the surface movement direction, and
      a second surface output detected from a second time-surface of the image bearing member positioned different from the potential-control toner pattern, the second time-surface positioned at a location shorter than one revolution upstream or downstream from the potential-control toner pattern in the surface movement direction,
   wherein the controller, to calculate a toner adhesion quantity of the potential-control toner pattern, determines whether to execute a first-surface output control, during which the reflection light detector detects at least the first time-surface of the image bearing member, or a second-surface output control, during which the reflection light detector detects only the second time-surface of the image bearing member, based on a use condition of the image forming apparatus.

2. The image forming apparatus according to claim 1, further comprising:
   a stop-time detector to measure stop time of the image forming apparatus,
   wherein the controller executes the first-surface output control when the measured stop time is longer than a predetermined value and executes the second-surface output control when the measured stop time is equal to or shorter than a predetermined value.

3. The image forming apparatus according to claim 1, further comprising:
   a temperature detector to measure ambient temperature inside or near the image forming apparatus,
   wherein the controller executes the first-surface output control when the measured ambient temperature is higher than a predetermined value, and executes the second-surface output control when the measured ambient temperature is equal to or lower than a predetermined value.

4. The image forming apparatus according to claim 1, further comprising:
   a temperature and humidity detector to measure ambient temperature and ambient humidity inside or near the image forming apparatus,
   wherein the controller executes the first-surface output control when the measured ambient temperature is higher than a predetermined value and the measured ambient humidity is higher than a predetermined value, and executes the second-surface output control under the condition other than when both the measured ambient temperature and ambient humidity are higher than a predetermined value.

5. The image forming apparatus according to claim 1, further comprising:
   a stop-time detector to measure stop time of the image forming apparatus; and a temperature detector to measure ambient temperature inside or near the image forming apparatus, wherein the controller executes the first-surface output control when the measured stop time is longer than a predetermined value and the measured ambient temperature is higher than a predetermined value, and executes the second-surface output control under the condition other than when both the measure stop time and the measured ambient temperature are higher than the respective predetermined values.

6. The image forming apparatus according to claim 1, further comprising:
a stop-time detector to measure stop time of the image forming apparatus; and
a temperature and humidity detector to measure ambient temperature and ambient humidity inside or near the image forming apparatus,
wherein the controller executes the first-surface output control when the measured stop time is longer than a predetermined value, the measured ambient temperature is higher than a predetermined value, and the measured ambient humidity is higher than a predetermined value, and executes the second-surface output control under the condition other than when all the measure stop-time, the measured ambient temperature, and the ambient humidity are higher than the respective predetermined values.

7. The image forming apparatus according to claim 1, further comprising:
a status detector to detect that an expendable is replaced,
wherein the controller determines whether to execute the first-surface output control or the second-surface output control, only when the detector detects that the expendable is replaced, and executes the second-surface output control other than when the status detector detects that the expendable is replaced.

8. The image forming apparatus according to claim 1, wherein the use condition of the image forming apparatus includes an idle time of the image forming apparatus.

9. An image forming apparatus comprising:
an endless rotary image bearing belt or roller having a surface to bear a toner image and a potential-control toner pattern;
an image forming belt or roller to form the toner image and the potential-control toner pattern onto the surface of the image bearing belt or roller;
a reflection light detector having a light source to emit light onto the surface of the image bearing belt or roller and the potential-control toner pattern formed on the image bearing belt or roller and a light-receiving element to detect the amount of light reflected from the potential-control toner pattern formed on the surface of the image bearing belt or roller as a toner attraction output, and the amount of light reflected from the surface of the image bearing belt or roller as a surface output; and
circuitry configured to detect toner information of the toner image based on the toner attraction output corresponding to the detected amount of light reflected from the potential-control toner pattern formed on the image bearing belt or roller, and the surface output corresponding to the amount of light reflected from the image bearing belt or roller, the circuitry configured to control the image forming belt or roller based on the detected toner information,
wherein the surface output comprises:
a first surface output detected from a first time-surface of the image bearing belt or roller positioned identical to the potential-control toner pattern, the first time-surface positioned one of an integer multiple of revolutions upstream from the potential-control toner pattern in a surface movement direction in which the surface of the image bearing belt or roller is moved and an integer multiple of revolutions downstream from the potential-control toner pattern in the surface movement direction, and
a second surface output detected from a second time-surface of the image bearing belt or roller positioned different from the potential-control toner pattern, the second time-surface positioned at a location shorter than one revolution upstream or downstream from the potential-control toner pattern in the surface movement direction,
wherein the circuitry, to calculate a toner adhesion quantity of the potential-control toner pattern, is configured to determine whether to execute a first-surface output control, during which the reflection light detector detects at least the first time-surface of the image bearing belt or roller, or a second-surface output control, during which the reflection light detector detects only the second time-surface of the image bearing belt or roller, based on a use condition of the image forming apparatus.

* * * * *